United States Patent [19]
Goto

[11] Patent Number: 5,779,656
[45] Date of Patent: Jul. 14, 1998

[54] LOAD REMOVING AND WALKING CAST FOR LOWER LEG AND METHOD OF MAKING THE SAME

[75] Inventor: Takeshi Goto, Kurume, Japan

[73] Assignee: Castec Corporation, Kurume, Japan

[21] Appl. No.: 820,000

[22] Filed: Mar. 18, 1997

Related U.S. Application Data

[63] Continuation of Ser. No. 567,171, Dec. 5, 1995, Pat. No. 5,649,898.

[30] Foreign Application Priority Data

Sep. 26, 1995 [JP] Japan ................... 7-270684

[51] Int. Cl.⁶ ............................................... A61F 5/00
[52] U.S. Cl. ........................................ 602/6; 602/9
[58] Field of Search ............................... 602/3, 4, 5, 6, 602/8, 9, 10, 11, 13

[56] References Cited

U.S. PATENT DOCUMENTS

| | | |
|---|---|---|
| 2,875,752 | 3/1959 | Lovich ........................... 602/10 |
| 4,565,250 | 1/1986 | Vasko ............................ 168/12 |
| 4,888,225 | 12/1989 | Sandvig et al. ................ 601/11 X |
| 5,002,047 | 3/1991 | Sandvig et al. ................ 602/8 |
| 5,520,621 | 5/1996 | Edenbaum et al. ............. 602/8 |
| 5,649,898 | 7/1997 | Goto ............................. 602/6 |

FOREIGN PATENT DOCUMENTS

| | | |
|---|---|---|
| 5-5116 | 1/1993 | Japan. |
| 7-289582 | 11/1995 | Japan. |

OTHER PUBLICATIONS

The Journal of Bone and Joint Surgery, American Volume, Jul. 1967.

*Primary Examiner*—Richard J. Apley
*Assistant Examiner*—Kim M. Lee
*Attorney, Agent, or Firm*—Jacobson, Price, Holman & Stern, PLLC

[57] ABSTRACT

A cast having a predetermined space between a sole of a foot held in the cast and a bottom of the cast. The foot can be moved slightly so that a pushing-up action by the bottom of the cast toward the sole of the foot can be prevented, thereby providing a load removing effect. If the thickness of the space is changed, the load removing effect may be controlled.

17 Claims, 8 Drawing Sheets

LOAD REMOVING AND WALKING CAST FOR LOWER LEG AND METHOD OF MAKING THE SAME

CROSS-REFERENCE TO RELATED APPLICATION

This is a continuing application (continuation-in-part) to Ser. No. 08/567,171 filed on Dec. 5, 1995, now U.S. Pat. No. 5,649,898.

TECHNICAL FIELD OF THE INVENTION

The present invention relates to lower leg load removing and walking casts used for treatment of tibial fractures, that is, casts applied to an affected leg, and a method of making the same.

DESCRIPTION OF RELATED ART

Figure 8:
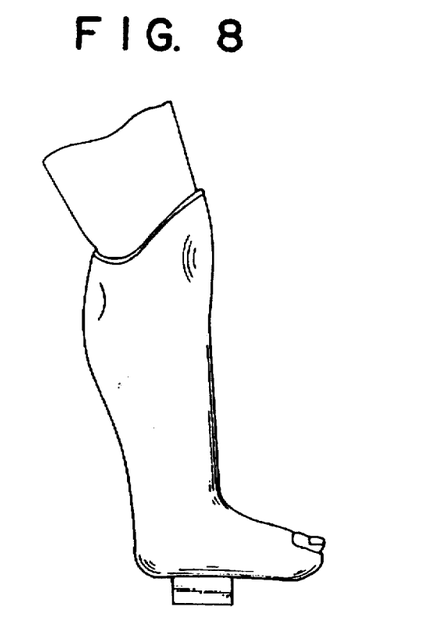
FIG. 8 is an explanatory view showing a conventional leg cast (PTB cast)

PTB casts (Patellar Tendon Bearing casts, so-called walking casts for lower leg) as seen in FIG. 8 has broadly been employed to treat tibial fractures (fracture of leg bone). This cast is used for bearing a patient's human body weight at pressured parts around the knee joints (portions of the patellar tendon and tibial condyle) shown with arrows in FIG. 9 in order to enable a knee joint to move or walk with a working cast after having treated the leg bone or at an early period after a surgical operation, thereby protecting the tibial fractured portion so as not to effect an excessive load thereon.

However, there are still many unknown matters in regard to the effects of removal of load which is a significant purpose of the cast, and accordingly not a few of the medical specialists feel dubious about the load removing effect. These specialists allow patients to rely on crutches for assisting the load removal over a long period of days even after having worn the cast for assisting the load removal.

In view of the above-mentioned circumstances, the inventor and associates used a dynamic foot pressure analysis system which was first introduced in Japan in 1992 and measured the load removing effect of the cast, and made studies on the actual load removing effects. Then, the load removing effect brought about by the prior cast was about only 30% of the patient's human body weight. This data tells us that 70% of the patient's weight is, when walking, burdened as a load on his fractured leg, and it was found that the load removing effect by the above-described broadly used cast was unsatisfied.

In an early healing period while the tibial fracture is not yet recovered, if the body weight is given upon a fractured limb, and the load removing effect is insufficient, the load force by the body weight is added as a disadvantageous pressure to the fractured part which results in causing curing difficulties such as a shortening deformity of the fractured part or delaying a healing of the fracture. However, the theoretical idea to allow the knee joint to move or to allow control of the walking as loaded at an early recovering time at which the cast aims, is very important for healing the tibial fracture. Therefore, if the cast decreases or enables to control as theoretically the load by the body weight to the fractured part of the leg, it may be expected that the usefulness thereby will become greater. In this sense, the necessity to improve the load removing effect of the cast has been highlighted as a focus of attention.

Prior art lower leg casts are also known where the cast portion surrounding the lower leg is short and does not reach the area adjacent the knee of a patient and the rear part adjacent the knee. See, Lovich patent No. 2,875,752 dated Mar. 3, 1959. Such casts cannot result in reducing the loads applied to the lower leg, even if a space were formed between the foot and bottom of the cast during the preparation of the cast, since the leg is not suspended or supported by the cast adjacent the knee. Such casts are not effective to reduce the load on the lower leg and are not as effective as even the prior art PTB casts described above.

SUMMARY OF THE INVENTION

The present invention has been designed to provide casts which excel in the load removing effect.

Figure 9:
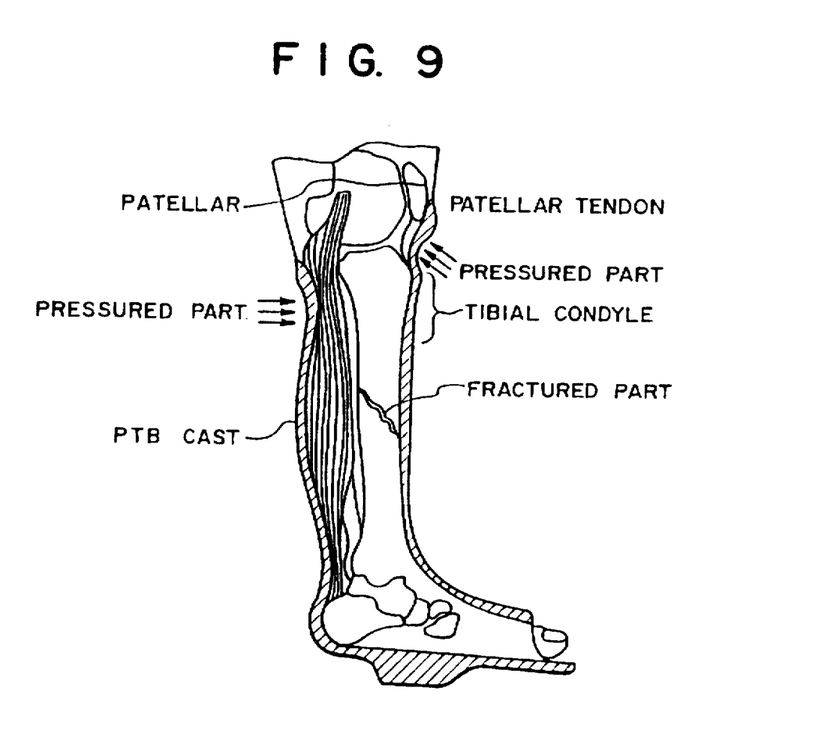
FIG. 9 shows parts aiming at supporting of a patient's human body weight (pressuring parts) in the above conventional leg cast (PTB cast), the supporting and pressurized portion of the cast also used in the above embodiments of the present invention.

The reason why a satisfactory load removing effect could not be obtained by means of the existing cast (of the type as shown in FIGS. 8 and 9) is that since the bearing of the body weight by the cast is insufficient, the load moves, when burdened, in the burdening direction of the leg within the cast, and the foot is pushed up on its sole by the bottom of the cast. The inventor and associates made by test various embodiments of casts for a purpose of improving the load removing effect of the cast for the tibial fracture, and made appreciations and studies on the load removing effect by the dynamic foot pressure analysis system. When a test was prepared for a cast such that a predetermined space is disposed between the sole of the foot and the bottom of the cast, the foot was, during walking, moved or played along the length of a shin bone (in the loading direction of the body weight) in the cast, whereby the push-up by the bottom of the cast toward the sole of the foot could be prevented, and it was found that the load removing effect was largely improved. For easily and exactly comprehending the principle of improving the load removing effect of the PTB cast, the below-mention example should be considered.

Imagine a morning-glory or trumpet shaped instrument. If a hand is inserted into the instrument at a flared mouth thereof, the arm is held by a conical interior of the instrument and can no further move ahead. Herein, the trumpet shaped instrument corresponds to the cast, and the arm corresponds to the affected leg. A force making the hand go farther corresponds to a load by the body weight. Namely, with respect to the conventional cast for fractured leg, the prior art intended that the leg was supported in the interior cavity of the cast which was presumed as the hollow conical column. However, since the cast and the leg are very imperfect figures as conical bodies, a dynamic bearing power is limited in itself, and the leg somewhat slides within the cast due to the body weight toward the sole of the foot. This sliding of the leg causes a push-up to, or reactive force upon, the sole of the foot by the cast, and the push-up hampers the load removing effect. Therefore, by forming a space between the sole of the foot and the bottom of the cast, the factor of hampering the load removing effect can be taken away even if the leg slides within the cast. Thus, a satisfactory load removing effect can be made available.

Stated another way, the load removing lower leg cast of the prior art supports, at an upper portion of the lower leg part of the cast surrounding the entire part of the patient's lower leg, only a portion of the reactive loading forces caused by the patient's walking, and all of the remaining part of the loading forces are received at the interior bottom of the cast, bearing against the sole of a patient's foot, so that a satisfactory load removing effect could not be provided. In accordance with the present invention, however, the reactive loading force at the interior bottom of the cast is removed by the space between the sole of the foot and the bottom of the cast, and is also received at the upper portion of the lower leg cast in accordance with the morning-glory or trumpet theory mentioned above, thereby obtaining the effect of canceling the absolute total amount of the reactive loading forces acting upon the foot and the tibial fractured part, that is, a sufficient load removing effect is achieved. Further, when the size of the space is changed, the load removing effect may also be controlled.

Thus, the present invention has been devised on the basis of a new finding, wherein a casting plaster is surrounded around the patient's leg such that a predetermined space is formed between the sole of the foot and the bottom of the cast. The cast prepared by the invention has excellent load removing and walking effect.

Figure 6A:
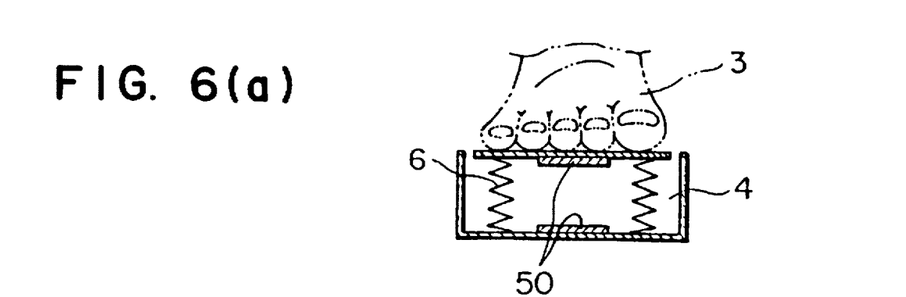
Figure 6B:
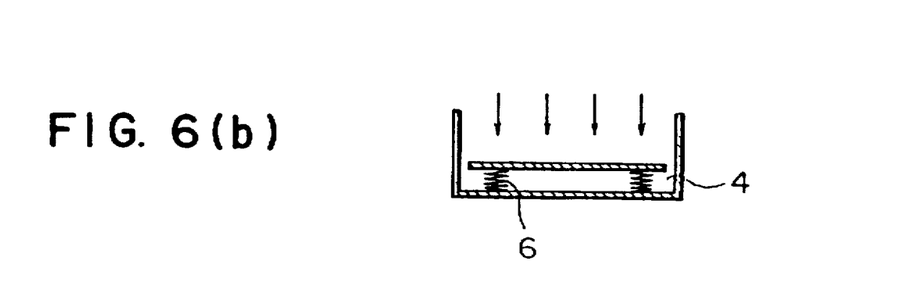
Figure 7A:
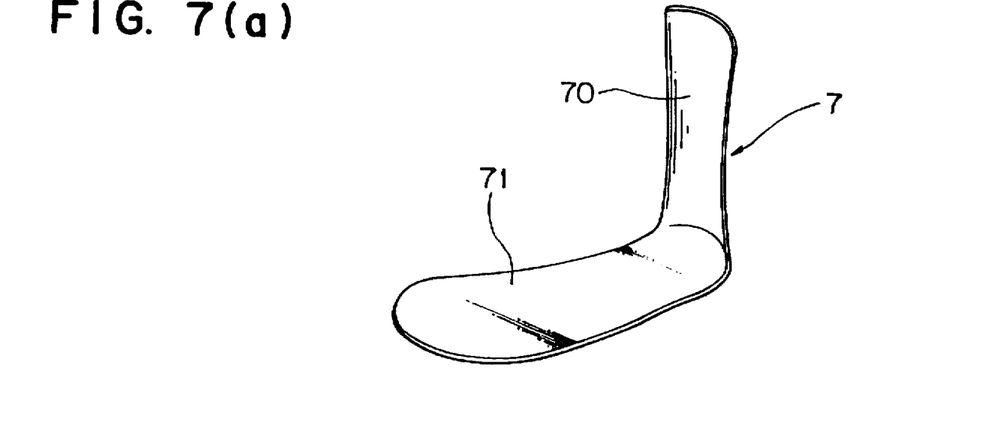
Figure 7B:
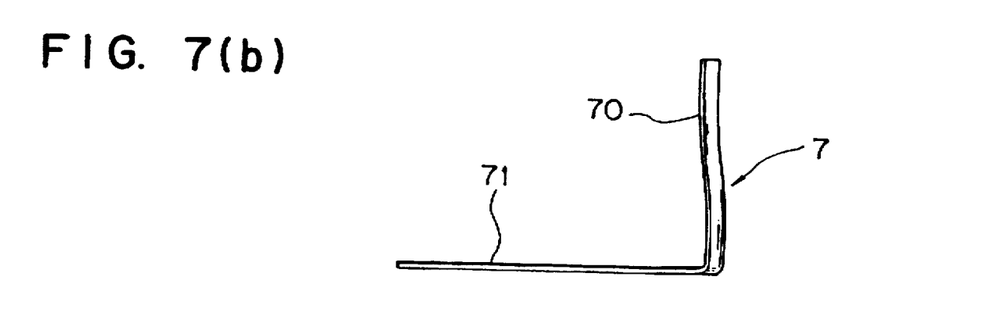

As the embodiments of the invention, there will be identified an embodiment fixed as it is attached to the sole of the foot (FIGS. 2, 5 and 6), and another embodiment held as it is attached to a heel, a portion of this embodiment being extended downward further than the heel (FIG. 7).

Further, when an elastic material is disposed in the space and is attached or placed adjacent to the sole of the foot, the thickness of the space after having been secured is varied when walking between the sole of the foot and the bottom of the cast, so that load removing effect may be controlled thereby.

Known material may be applicable as the elastic member if it expands and contracts when walking in response to even a slight load, such as a sponge, a soft rubber or a bellows composed of a soft synthetic resin. The wider the space, the better the load absorbing efficiency, and so the bellows bag or the sponge are preferable.

The cast is formed with the predetermined space therebetween. If the patient walks with the leg cast, the foot can be moved or played in the space along the length of the shin bone (in the loading direction) within a predetermined range. This play absorbs an impact force or the load reactive force which would otherwise adversely influence the fractured bone of the leg, and thus a satisfactory load removing effect is made available.

BRIEF DESCRIPTION OF THE DRAWINGS

FIGS. 1 (a)–(c) show a first embodiment, in which FIG. 1 (a) is a front view of this embodiment, FIG. 1 (b) is a plan view of the same, and FIG. 1 (c) is a side view thereof.

FIGS. 2 (a)–(c) show the condition of the cast provided by the first embodiment in use, in which FIG. 2 (a) is a front view of this condition, FIG. 2 (b) is a plan view of the same, and FIG. 2 (c) is a side view thereof.

FIGS. 3 (a)–(c) show the bellows bag, in which FIG. 3 (a) is a front view of this embodiment, FIG. 3 (b) is a plan view of the same, and FIG. 3 (c) is a side view thereof FIGS. 4 (a)–(b) show expansion and contraction of the bellows bag, in which FIG. 4 (a) is a case of the former, and FIG. 4 (b) is a case of the latter.

FIGS. 5 (a)–(c) show a second embodiment in which FIG. 5 (a) is a cross-sectional front view of this embodiment, FIG. 5 (b) is a plan view of the same, and FIG. 5 (c) is a side view thereof FIGS. 6 (a)–(b) show a third embodiment in which FIG. 6 (a) is a cross-sectional front view illustrating an expansion of the spring, and FIG. 6 (b) is a view illustrating a contraction of the same.

FIGS. 7 (a)–(c) shows a fourth embodiment in which FIG. 7 (a) is a perspective view of this embodiment, FIG. 7 (b) is a side view of the same, and FIG. 7 (c) is a view showing the use thereof

In the drawings of FIGS. 1 through 9, the reference numeral 1 is the cast body, 2 is a bellows bag as an elastic member made of a soft resin, 3 is a foot, 4 is a space defined between the sole of the foot and the bottom of the cast by means of the present inventive instrument, 5 is a sponge, 6 is a spring, 7 is a protecting plate, 10 is a bottom of the cast, and 20 is a protecting case made of a hard resin.

PREFERRED EMBODIMENTS OF THE INVENTION

Reference will be made to the steps of making the cast by means of the instruments exemplified herein. FIG. 7 shows a most basic embodiment of this invention, from which other embodiments are derived. However for easy understanding of the invention, explanation will be made with FIG. 7 as a fourth embodiment.

Figure 1A:
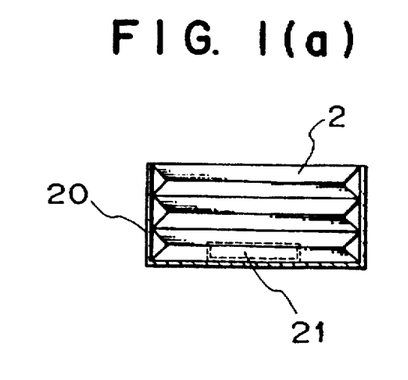
Figure 1B:
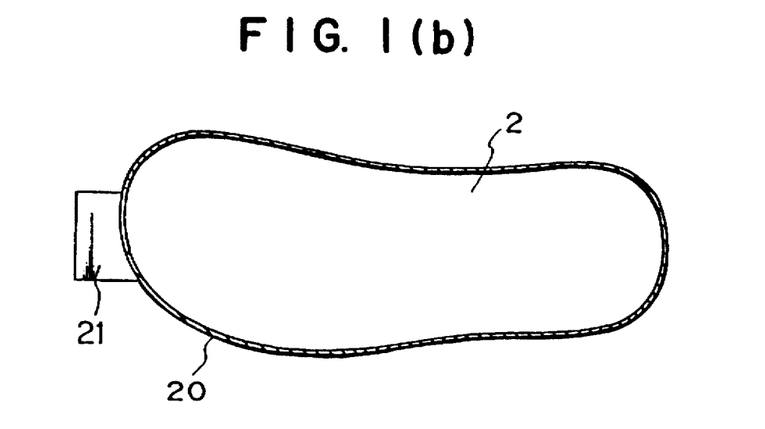
Figure 1C:
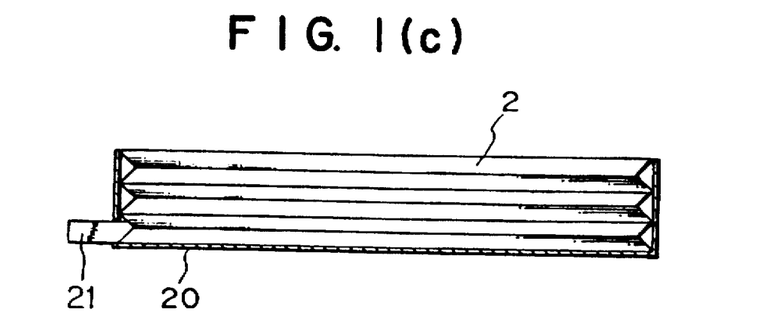
Figure 3A:
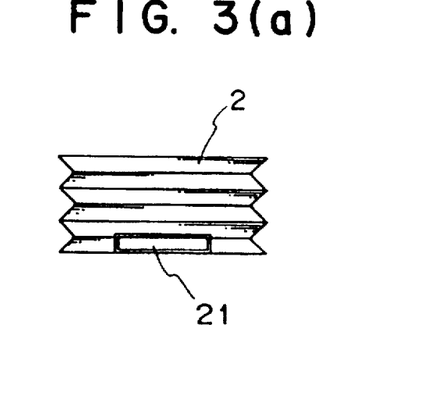
Figure 3B:
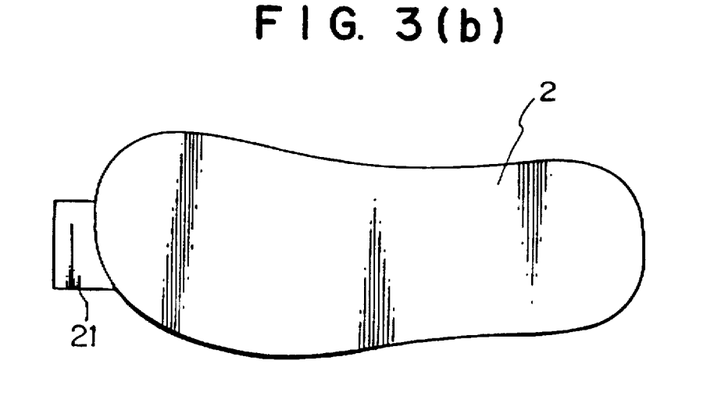
Figure 3C:
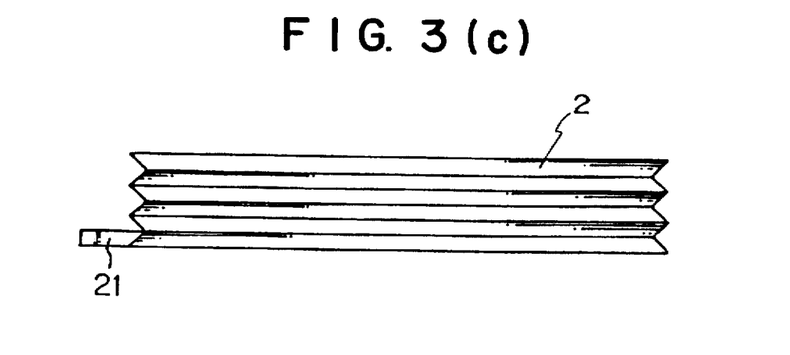
Figure 4A:
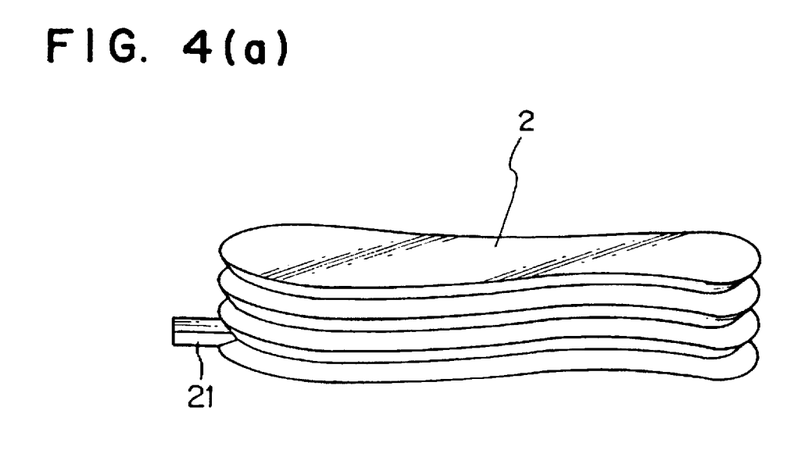
Figure 4B:
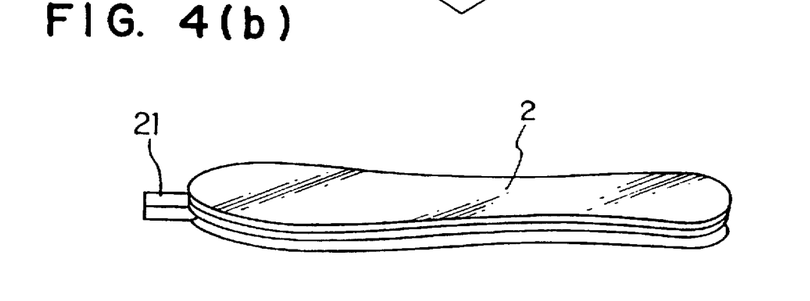

The bellows bag 2 is closed at an air hole 21 as seen in FIG. 3 and is disposed within a protecting case 20 comprising a hard resin as illustrated in FIG. 1. A foot 3 is then put on the bellows bag 2, followed by wrapping the casting plaster on the foot in an ordinary sequence and hardening it. When wrapping and hardening the casting plaster, a considerable pressure is burdened on the bellows bag 2, however it may perfectly maintain its shape against the pressuring force, since it is placed within the hard protecting case 20 and the air hole 21 is tightened or closed. When the air hole 21 is opened after the plaster 1 is solidified, the bellows bag 2 is made to freely expand and contract as is seen in FIG. 4, and the load removing and walking cast having excellent load removing effect is accomplished.

The protecting case 20 serves to protect the soft and elastic bellows bag 2 against the cast 1 wrapped around the patient's leg, and due to this protecting service, the bellows bag 2 may expand and contract vertically (along the length of the shin bone) even by a weak pressure within the cast 1.

Figure 2A:
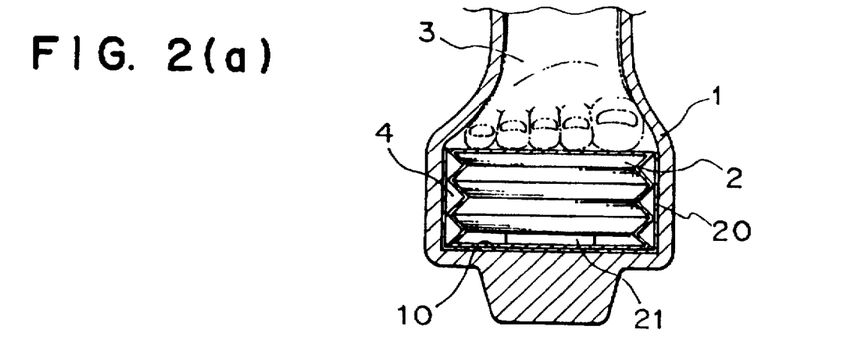
Figure 2B:
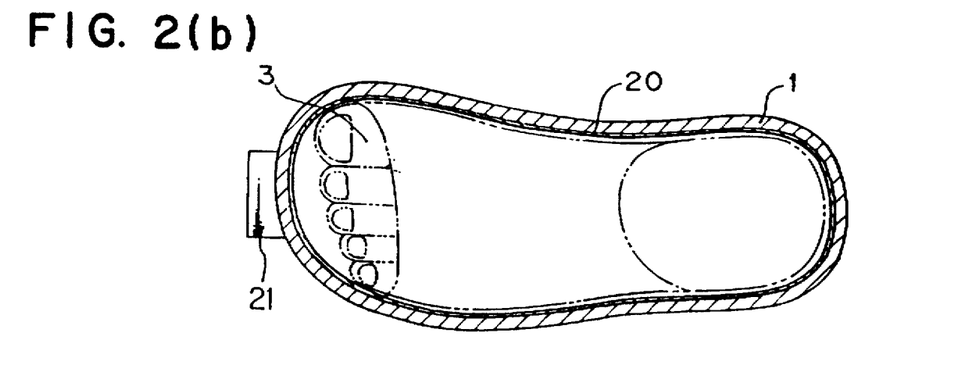
Figure 2C:
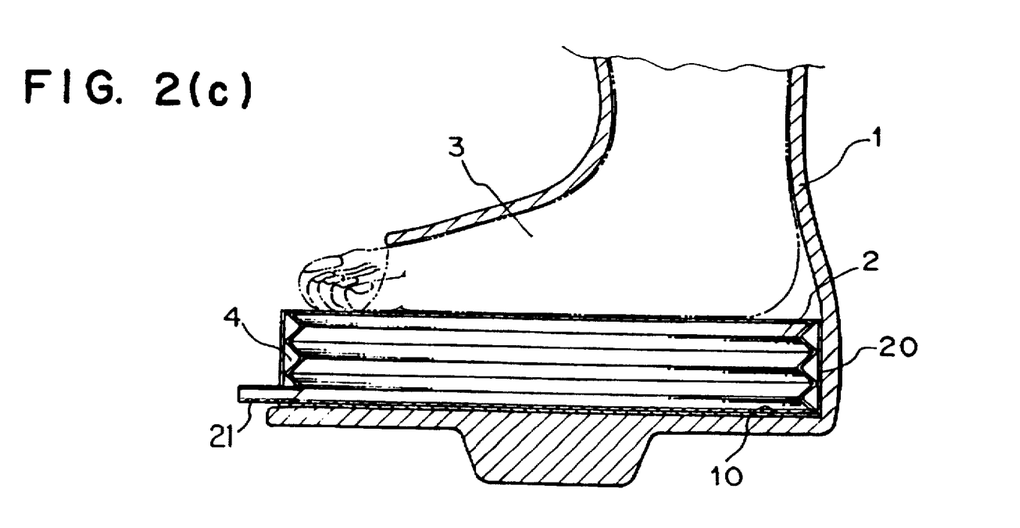

As shown in FIG. 2, the space 4 exists between the sole of the foot 3 and the bottom 10 of the cast 1, and the protecting case 20 made of the hard synthetic resin is disposed in the space 4, within which the bellows bag 2 is placed. The bellows bag 2 communicates with the exterior through the air hole 21, and expands and contracts in response to moving of the foot as the patient walks as burdened. Therefore, when walking with the present cast 1, the bellows bag 2 placed in the space 4 is pressured and easily shrinked, and the foot 3 may moderately or slightly move along the length of the shin bone (in the loading direction) within the space 4, and this moving partially absorbs the loading force by the walking burden. Thus, as will be later exemplified, a sufficient load removing effect may be provided.

The load removing and walking cast 1 of the embodiment described above, and indeed of each of the embodiments of the invention described herein, extends downward from the knee region, and is shaped at the knee region in a manner that catches around the knee and its adjacent parts. The leg of a patient is thus suspended by the shape of the cast with respect to the leg together with the pressure of the cast with respect to the leg adjacent the front and rear parts of the knee. That is, due to the shape of the cast and the catching or holding of the lower leg at the knee and the rear part of the knee by the cast, the leg is suspended and does not slide down, or slides down only slightly less than the distance of the space that is formed between the sole of the foot and the interior bottom portion of the cast. The suspension of the lower leg at the knee region in accordance with the teachings of the inventive cast as described, along with the maintaining of a sufficient space between the sole of a foot and the interior bottom portion of the cast, is an important feature of the present invention to remove or substantially lessen the reactive forces caused by walking upon the lower leg.

Figure 5A:
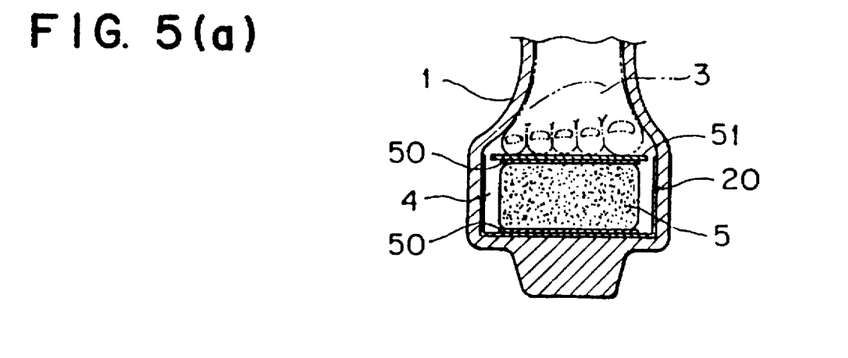
Figure 5B:
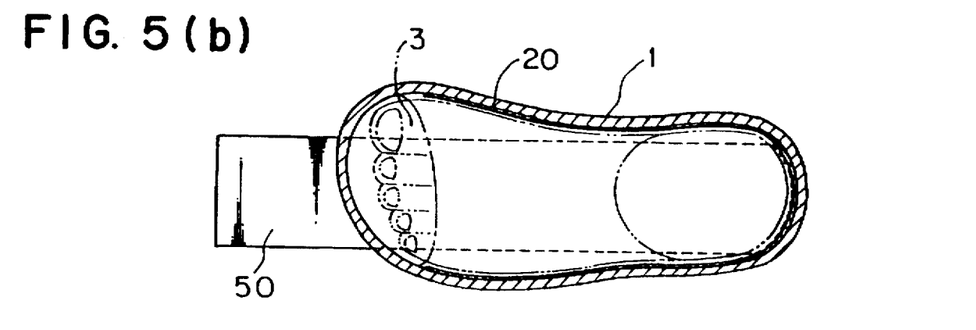
Figure 5C:
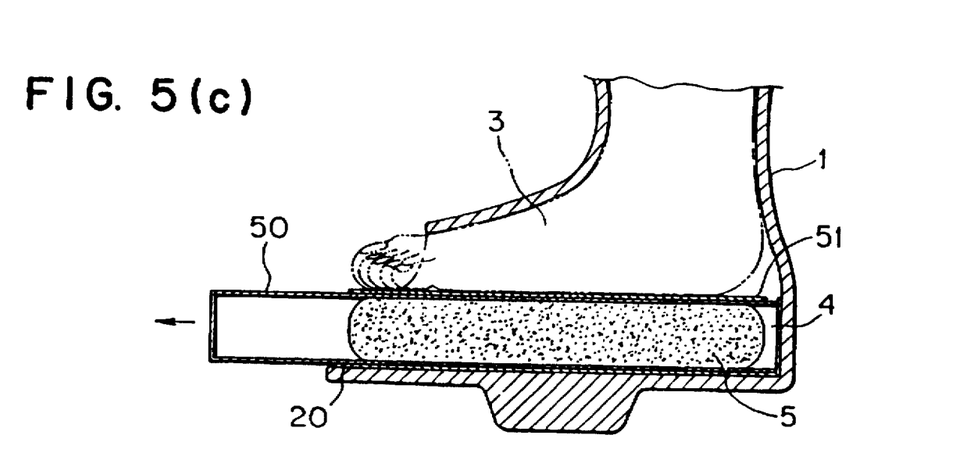

FIG. 5 illustrates a second embodiment, and FIG. 6 shows a third embodiment, and these embodiments employ the sponge and the spring respectively, in place of the bellows bag 2 of the first embodiment.

A further explanation will be made to the process of preparing or making the cast of the second embodiment. A space holding or maintaining instrument 50 is inserted into a front opening part of the protecting case 20, said space holding instrument being of a rectangle opening one of vertical sides in cross section (Z1) and holding a sponge 5 with its upper and lower sides. A bottom plate 51 is placed on an upper plate of the space holding instrument 50, and the foot 3 is put on the bottom plate 51, followed by wrapping the casting plaster around the patient's foot by the ordinary means.

The space holding instrument 50 is removed after the plaster has been solidified. Then, the space 4 appears between the sole of the foot 3 and the bottom of the cast 1, and the sponge 5 elastically acts within the space 4. Thus, the cast is completed. The process of the third embodiment is similar to the second embodiment, in which depending upon the space holding instrument 50, the space 4 appears, similarly therebetween, and a spring 5 expands and contracts within the space 4.

Also in the use of the cast 1 produced by these embodiments, when walking, the foot 3 may moderately move or slide slightly within the cast along the length of the shin bone (in the loading direction), so that the loading force caused by the walking burden is fully absorbed.

Figure 7C:
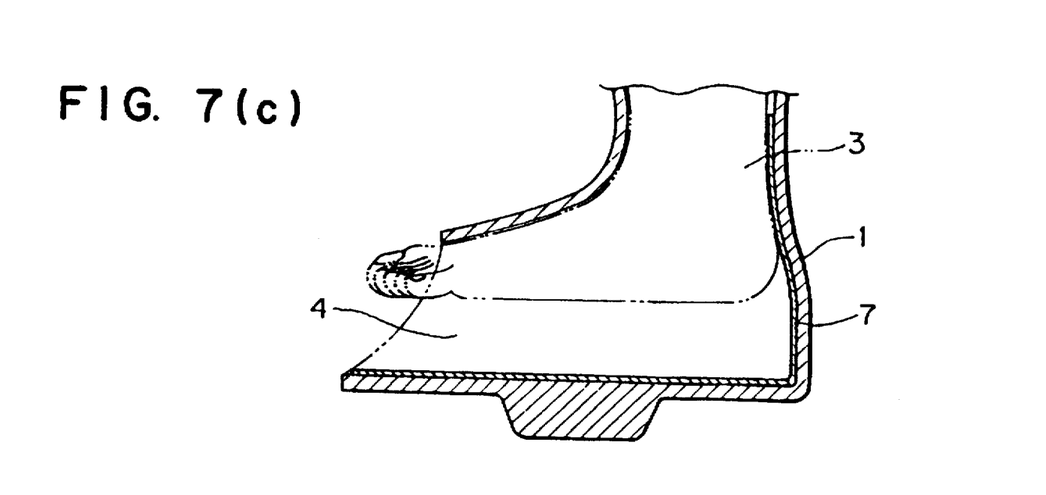

FIG. 7 illustrates a fourth embodiment. As shown in FIG. 7(c), a space is formed between the sole of a patient's foot and the interior bottom base portion of the cast. A similar space is also formed in the first to third embodiments, in which, however, the elastic member is interposed in the space so as to control the load removing and walking effect.

The substantially L-shaped member 7 is used to form the space between the sole of the foot 3 and the bottom of the cast 1 during the preparation of the cast. The member or protecting plate 7 of this embodiment is L-shaped in cross section or a bent plate member comprising a side 70 contacting a heel of the foot, and slightly above near the calf, and a bottom 71 forming a substantially planar base and contacting the bottom of the cast 1 after the cast is solidified.

The process for preparing the cast of this embodiment brings the heel to the side 70 such that a space is formed between the sole of the foot 3 and the bottom 71 of the protecting plate, and it is sufficient to wrap and solidify the casting plaster under a condition that the lower portion of the side 70 extends further downward than the heel so as to form the space 4.

In this embodiment a cast like a morning-glory or trumpet is formed leaving the space between the sole of the foot and the bottom of the protecting plate 7 as seen in FIG. 7(c). The sole of the foot does not contact the bottom 71 due to suspending the lower leg by holding the lower leg at the knee and its adjacent parts, so that the space 4 is maintained during walking. The reactive forces caused by walking are taken up through the cast and are at least partially borne at the upper portions of the lower leg adjacent the knee (front and rear), as previously described.

The embodiment of FIG. 7 does not employ any intermediates such as the bellows, the spring or the sponge between the sole of the foot and the bottom of the cast, however the cast of this embodiment can also make a space for avoiding the push-up, and bring about the satisfied load removing and walking effect by moving of the foot within the space while walking.

With respect to the above embodiments, the load removing and walking effects were tested using the dynamic foot pressure analysis system in comparison with the prior cast as shown in FIGS. 8 and 9.

The prior PTB cast of FIGS. 8 and 9 showed that the load removing effect was only 30.5% of the human body weight, while the load removing and walking effect of the present invention when the cast having the space distance of 1 cm (10 mm) was 55.9%, that in a case of 1.5 cm (15 mm) was 65.8%, that of 2.5 cm (25 mm) was 93.7%, and that of 3 cm (30 mm) was 100% which was the perfect load removing and walking effect.

As explained at length, the leg casts provided by means of the invention bring about remarkable results to largely improve the load removing and walking effect.

It should be appreciated that the cast of the present invention can extend above the knee and may extend to the hip. Such a cast may support the hip bone and provide load removal upon the entire leg including load removal at the thigh.

It may be appreciated that the embodiments using the elastic member provide for controlling the load removing effect. The elastic member which may vary the space, controls the load removing effect. That is, for healing the tibial fracture, a sufficient load removing effect is required immediately after suffering the tibial fracture. It is said that a callous appears around the fractured part as time goes on, and a moderate burden upon the fractured part advantageously acts on the bone formation. However, the prior art cast did not bring about a sufficient load removing effect required at the beginning period of curing the fractured bone, and, further, it was impossible to control the load removing effect in accordance with the curing progress. In contrast, in the present invention, as above exemplified, the load removing effect can be varied by changing the thickness of the elastic member. Therefore, if using the elastic members of different thicknesses in response to the curing progress, the load removing effect may be controlled, and it may be served as an optimum curing instrument.

I claim:

1. A method for forming a load removing and walking cast about a lower leg of a patient comprising the steps of positioning a substantially L-shaped member having a substantially planar base and an upstanding heel-contacting plate member adjacent a lower leg of a patient such that the upstanding plate member is in contact with the patient's heel of the foot and the substantially planar base is spaced away from the sole of a patient's foot to define a spatial void therebetween, applying a casting plaster about the lower leg and foot of a patient to form a cast having an interior bottom base portion cast adjacent said substantially planar base and including a leg surrounding portion that surrounds, supports, and suspends the lower leg of a patient at the knee and its adjacent parts so as to maintain a spatial void between the sole of a patient's foot and the interior bottom base portion, and allowing the casting plaster to solidify.

2. A method for forming a load removing and walking cast about a lower leg of a patient comprising the steps of positioning an elastic member adjacent the sole of a patient's foot, applying a casting plaster about the lower leg and foot of a patient and about the elastic member to form a cast having an interior bottom base portion cast spaced away from the sole of a patient's foot with the elastic member between the sole of a patient's foot and the interior bottom base portion, and including a leg surrounding portion that surrounds, supports, and suspends the lower leg of a patient at the knee and its adjacent parts so as to maintain a spacing between the sole of a patient's foot and the interior bottom base portion, and allowing the casting plaster to solidify.

3. The method as claimed in claim 2 wherein said elastic member comprises a bellows bag.

4. The method as claimed in claim 2 wherein said elastic member is a sponge.

5. The method as claimed in claim 2 wherein said elastic member is a spring.

6. The method as claimed in claim 2 further comprising the steps of disposing said elastic member within a protective casing, said protective casing including a bottom portion and sidewall portions, said casing being open at the top, and positioning the elastic member and protective casing adjacent the sole of the patient's foot prior to the applying step.

7. A load removing and walking lower leg cast adapted to surround and support the lower leg of a patient comprising a plaster cast leg surrounding portion and a plaster cast bottom portion, a substantially L-shaped member having a substantially planar base and an upstanding plate member, said planar base lying upon said plaster cast bottom portion and an upper portion of said upstanding plate member in contact with the patient's heel portion of the foot to maintain a spatial void between said plaster cast bottom portion and the sole of a patient's foot during the imposition of reactive loading forces upon the cast during walking so as to reduce the loading forces acting upon a patient's lower leg.

8. A load removing and walking lower leg cast adapted to surround and support the entire lower leg and foot of a patient and having a length that extends downward from at least the region adjacent the knee of a patient to a position below the sole of a patient's foot so as to define a space between the sole of a patient's foot and an interior bottom portion of said cast, said cast including means for supporting and suspending the lower leg of a patient at an upper portion of the lower leg of a patient and for maintaining the sole of a patient's foot out of load bearing contact with said interior bottom portion of said cast, wherein at least part of any reactive loading forces upon the cast caused by walking of the patient are borne at upper portions of the lower leg and wherein any downward movement of the lower leg portion within the cast during walking is less than the space between the sole of the patient's foot and the interior bottom portion of said cast.

9. The load removing and walking cast of claim 8 wherein said means for supporting and maintaining enables downward movement of the lower leg of a patient within the cast of approximately 10 mm.

10. The load removing and walking cast of claim 8 wherein said space between the sole of a patient's foot and the interior bottom portion of said cast is at least 10 mm.

11. The load removing and walking cast of claim 8 further comprising an elastic member disposed in the space between the sole of the foot and said interior bottom portion of said cast.

12. The load removing and walking cast as claimed in claim 11 wherein said elastic member comprises a sponge.

13. The load removing and walking cast of claim 11 wherein said elastic member comprises a spring.

14. The load removing and walking cast of claim 8 further comprising a space maintaining means for maintaining a space between the sole of a patient's foot and the interior bottom portion of said cast during formation of said cast about the lower leg of a patient.

15. The load removing and walking cast of claim 14 wherein said space maintaining means includes a substantially L-shaped member having a substantially planar base and an upstanding heel-contacting plate member, wherein the interior bottom portion of said cast is formed adjacent to and in contact with said substantially planar base.

16. The load removing and walking cast of claim 14 wherein said space maintaining means is removable from said cast after formation of said cast.

17. The load removing and walking cast of claim 16 wherein said space maintaining means is substantially U-shaped in cross section and disposed between the interior bottom base portion and the sole of the patient's foot, said space maintaining means being positioned adjacent to the sole of a patient's foot during formation of said cast in order to set and maintain a predetermined space and being removable therefrom after the cast is completed.

* * * * *